United States Patent
Luo et al.

(10) Patent No.: US 12,083,197 B2
(45) Date of Patent: Sep. 10, 2024

(54) PET CLEANING KIT

(71) Applicant: HICC PTE. LTD., Singapore (SG)

(72) Inventors: Weilun Luo, Shenzhen (CN); Rui Wang, Shenzhen (CN); Guoqiao Bi, Shenzhen (CN)

(73) Assignee: HICC PTE. LTD., Singapore (SG)

( * ) Notice: Subject to any disclaimer, the term of this patent is extended or adjusted under 35 U.S.C. 154(b) by 255 days.

(21) Appl. No.: 17/689,518

(22) Filed: Mar. 8, 2022

(65) Prior Publication Data

US 2022/0287930 A1 Sep. 15, 2022

Related U.S. Application Data

(60) Provisional application No. 63/158,690, filed on Mar. 9, 2021.

(51) Int. Cl.
*A61K 8/20* (2006.01)
*A01K 13/00* (2006.01)
(Continued)

(52) U.S. Cl.
CPC .............. *A61K 8/20* (2013.01); *A01K 13/003* (2013.01); *A45D 34/04* (2013.01); *A61Q 17/005* (2013.01); *A61Q 19/10* (2013.01); *B65D 81/3266* (2013.01); *A45D 2200/10* (2013.01); *A61K 2800/87* (2013.01); *A61K 2800/882* (2013.01)

(58) Field of Classification Search
CPC ............. A61K 8/20; A61K 2800/87; A61K 2800/882; A01K 13/003; A45D 34/04; A45D 2200/10; A61Q 17/005; A61Q 19/10; B65D 81/3266; B65D 75/5805;
(Continued)

(56) References Cited

U.S. PATENT DOCUMENTS

| | | | | |
|---|---|---|---|---|
| 1,984,183 A | * | 12/1934 | Gillespie | A41D 19/02 2/169 |
| 2002/0192268 A1 | * | 12/2002 | Alwattari | A61Q 19/10 424/443 |

(Continued)

FOREIGN PATENT DOCUMENTS

| | | |
|---|---|---|
| JP | H09216665 A | 8/1997 |
| JP | 2005145543 A | 6/2005 |
| JP | 2010143609 A | 7/2010 |

OTHER PUBLICATIONS

Search Report from European Patent Application No. 22159769.3 dated Aug. 2, 2022 (8 pages).

(Continued)

*Primary Examiner* — Donnell A Long
(74) *Attorney, Agent, or Firm* — Westbridge IP LLC (57) ABSTRACT

A fluid treatment kit comprises a flexible plastic container defining a first compartment and a second compartment. The first compartment contains a treating fluid. The second compartment contains at least one applicator. A breakable seal is disposed between the first compartment and the second compartment. The breakable seal is breakable to allow the treating fluid to flow into the second compartment and contact with the applicator. The applicator comprises liquid-absorbing materials and absorbs the treating fluid. The user then opens the flexible plastic container to remove the applicator and uses the applicator for the treatment of the pet.

12 Claims, 9 Drawing Sheets

(51) Int. Cl.
*A45D 34/04* (2006.01)
*A61Q 17/00* (2006.01)
*A61Q 19/10* (2006.01)
*B65D 81/32* (2006.01)

(58) Field of Classification Search
CPC ........... B65D 81/3261; A61L 2202/181; A61L 2/0088; C01B 11/04
See application file for complete search history.

(56) References Cited

U.S. PATENT DOCUMENTS

| | | |
|---|---|---|
| 2006/0124476 A1 | 6/2006 | Sivakumar et al. |
| 2010/0140119 A1 | 6/2010 | Katsuki |
| 2015/0000609 A1* | 1/2015 | Frye .................... A01K 13/001 119/625 |
| 2019/0023477 A1 | 1/2019 | Kelley et al. |
| 2020/0085982 A1 | 3/2020 | Compo et al. |
| 2020/0196825 A1 | 6/2020 | Kelley, Jr. et al. |

OTHER PUBLICATIONS

First Office Action issued in counterpart Chinese Patent Application No. 202210221687.6, dated Dec. 18, 2023.

* cited by examiner

PET CLEANING KIT

CROSS-REFERENCED TO RELATED APPLICATION

This application claims priority to and all benefit of U.S. Provisional Patent Application Ser. No. 63/158,690, filed on Sep. 9, 2021, for PET CLEANING KIT, the entire disclosure of which is fully incorporated herein by reference.

TECHNICAL FIELD

The present application is directed to apparatuses used in pet care, and more particularly to fluid treatment kits utilizing a treating fluid such as hypochlorous acid solution.

BACKGROUND

Hypochlorous acid can form non-toxic, colorless, and substantially odorless solutions suitable for sterilization of skin and mucous membranes. Hypochlorous acid solution can be used in pet cleaning products. However, hypochlorous acid is highly reactive and unstable. Hypochlorous acid reacts or decomposes when in contact with organic matters for a prolonged period of time, decreasing the cleaning effectiveness of the hypochlorous acid solution. Current pet cleaning products utilizing hypochlorous acid include products similar to alcohol wipes, which comprise hypochlorous acid solution absorbed in non-woven fabrics. In such products, hypochlorous acid is allowed to contact and react with the fabrics from the time of manufacture and packaging. As a result, the cleaning effectiveness continuously decreases, and the sterilization effectiveness of the cleaning product cannot be ensured.

SUMMARY

The present disclosure provides a fluid treatment kit comprising a flexible plastic container. The flexible plastic container defines a first compartment and a second compartment. The first compartment contains a treating fluid. The second compartment contains at least one applicator. A breakable seal is disposed between the first compartment and the second compartment. The breakable seal is breakable to allow the treating fluid to flow into the second compartment. The at least one applicator comprises a liquid-absorbing material that absorbs the treating fluid flowing into the second compartment.

DETAILED DESCRIPTION

The invention now will be described more fully hereinafter through reference to various embodiments. These embodiments are provided so that this disclosure convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", and "the", include plural referents unless the context clearly dictates otherwise.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure, however, such values and ranges are not to be construed in a limiting sense and are intended to be critical values or ranges only if so expressly stated. Parameters identified as "approximate" or "about" a specified value are intended to include both the specified value and values within 10% of the specified value, unless expressly stated otherwise. Further, it is to be understood that the drawings accompanying the present disclosure may, but need not, be to scale, and therefore may be understood as teaching various ratios and proportions evident in the drawings. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated.

Figure 1:
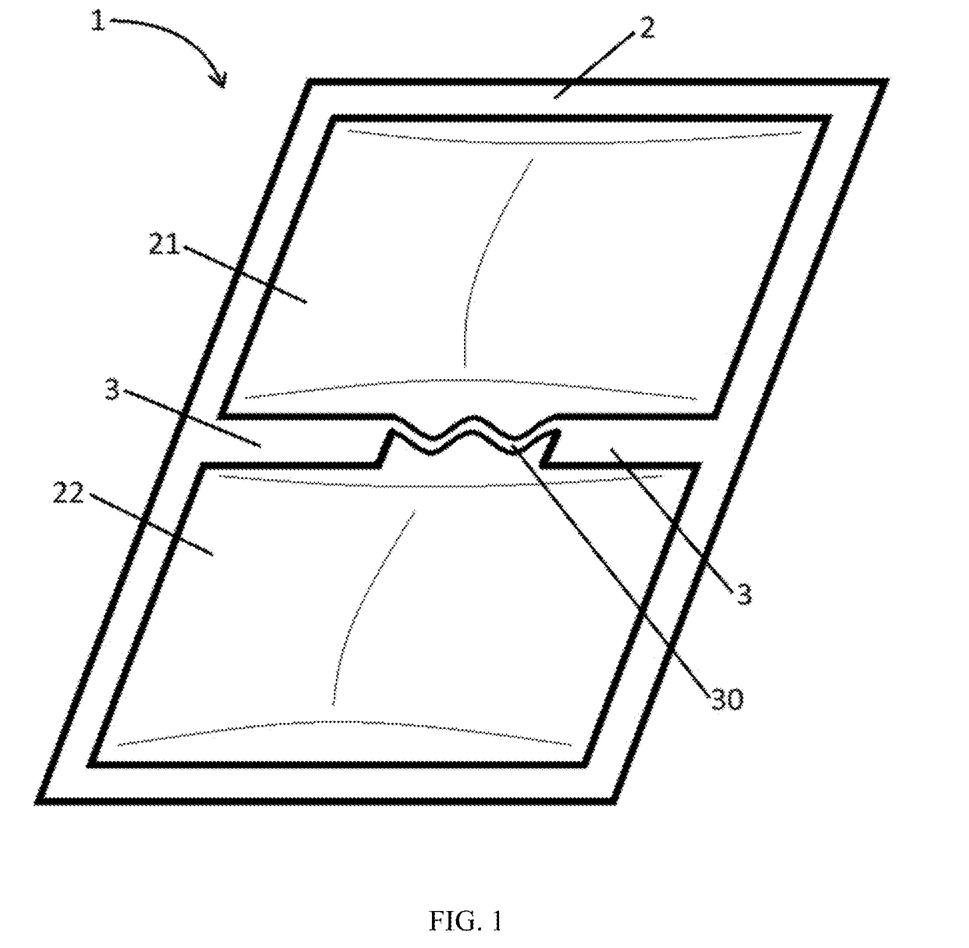
FIG. 1 is a perspective view of a fluid treatment kit according to an exemplary embodiment.
Figure 2:
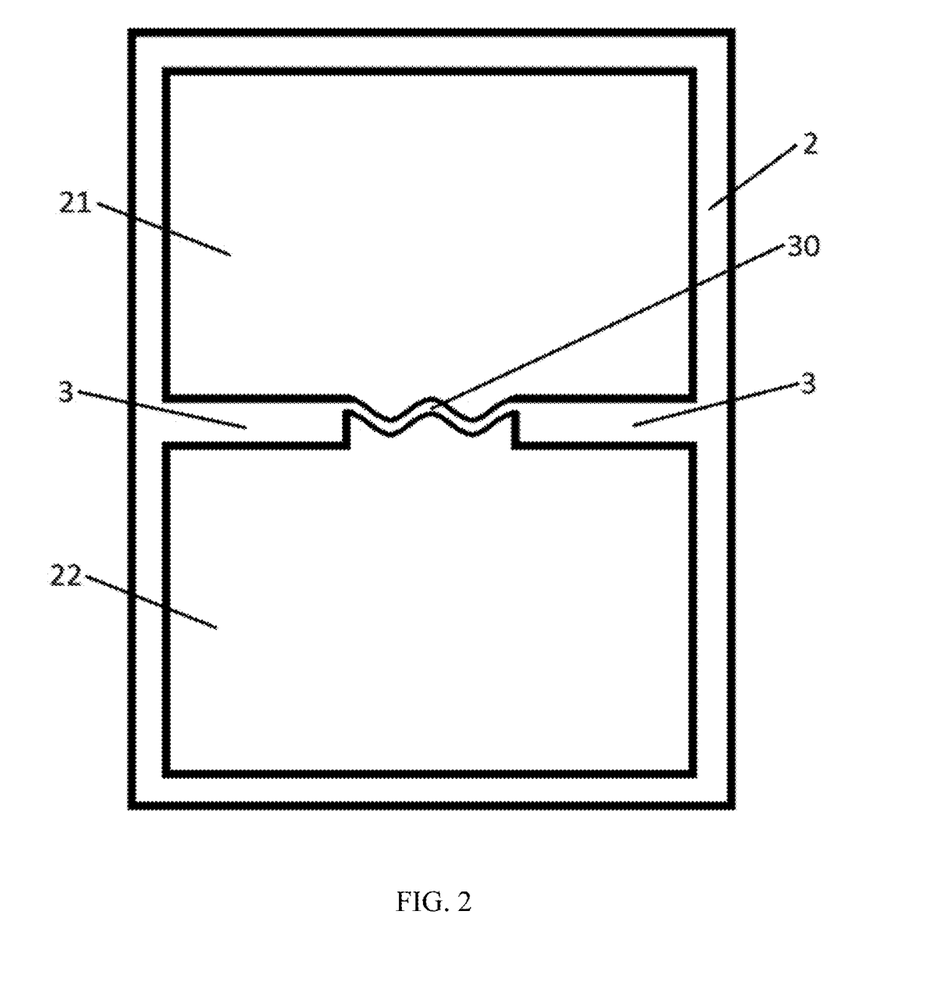
FIG. 2 is a top plan view of the fluid treatment kit shown in FIG. 1.
Figure 3:
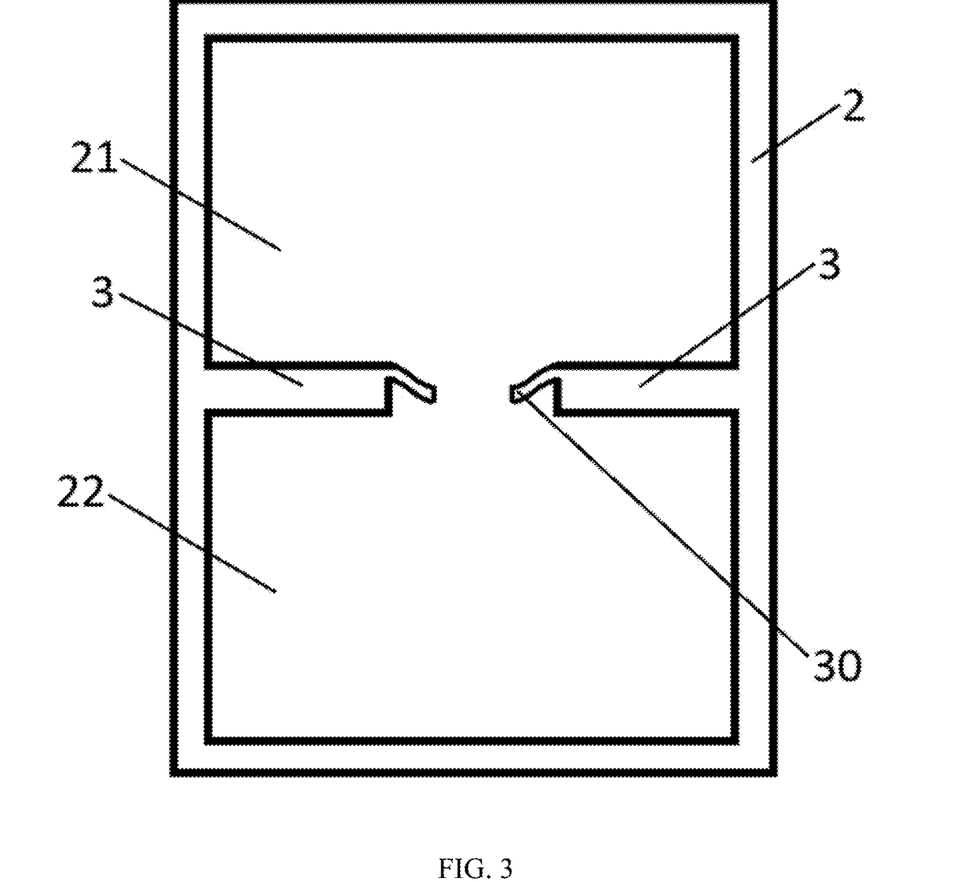
FIG. 3 is a top plan view of the fluid treatment kit shown in FIGS. 1-2, where a breakable seal of the fluid treatment kit is broken.

As illustrated in FIGS. 1-4, in some embodiments, a fluid treatment kit 1 comprises a flexible plastic container 2. The flexible plastic container 2 defines a first compartment 21 and a second compartment 22. The first compartment 21 contains a treating fluid. In some embodiments, the treating fluid is a hypochlorous acid solution. The second compartment 22 contains at least one applicator 4. A breakable seal 30 is disposed between the first compartment 21 and the second compartment 22. As illustrated in FIG. 3, the breakable seal 30 is breakable to allow the treating fluid to flow into the second compartment 22 and contact with the applicator 4. The applicator 4 comprises liquid-absorbing materials and absorbs the treating fluid. The user then opens the flexible plastic container 2 to remove the applicator 4, and uses the applicator 4 for the treatment of the pet. For example, the applicator 4 can be used for cleaning and disinfecting the pet, treating the wounds of the pet, and caring for the pet's skin.

Prolonged contact with the at least one applicator 4 may cause the reaction and decomposition of the active ingredients in the treating fluid. For example, hypochlorous acid may react or decompose when in contact with non-woven fabrics comprising polymer fibers. In the fluid treatment kit 1, the treating fluid is stored individually in the first compartment 21, and separately from the at least one applicator 4. As such, the reaction and decomposition of the active ingredients in the treating fluid is suppressed prior to the use of the fluid treatment kit 1. As result, the treatment effect of the fluid treatment kit 1 is maintained, and the shelf life of the fluid treatment kit 1 is extended.

Moreover, some pets dislike contacting water, such as taking a shower or bath. The fluid treatment kit 1 allows the user to treat the pet by wiping with the at least one applicator 4, which does not involve contacting the pet with a large amount of water. In some embodiments, the applicator 4 is formed into a glove, allowing the user to wear the applicator 4 on a hand while treating the pet. As such, the treatment can be done by movements which the pet is accustomed to, such as petting, wiping, or rubbing movements. Compared with pet treatments performed by pet grooming services, the fluid treatment kit 1 provides the user with opportunities to develop relationship with the pet by interacting with the pet during the use of the fluid treatment kit 1. The fluid treatment kit 1 allows the user to pet, wipe, or rub the pet with the applicator 4 as a method of daily cleaning, providing an alternative to bathing the pet with water.

As illustrated in FIGS. 1-4, in some embodiments, the flexible plastic container 2 may comprise two pieces of plastic sheets. The first compartment 21 and the second compartment 22 are defined between two pieces of plastic sheets. The two pieces of plastic sheets are sealed with each other by, for example, adhesives or heat sealing, such that the first compartment 21 and the second compartment 22 are hermetically sealed compartments. In some embodiments, as illustrated in FIGS. 1-4, the first compartment 21 and the second compartment 22 are defined by frangible seals formed by two pieces of plastic sheets. The flexible plastic container 2 may comprise any flexible plastic material suitable for storing the treating fluid. For example, in some embodiments, the treating fluid is a hypochlorous acid solution, and the flexible plastic container 2 comprises LDPE, HDPE, polypropylene, PET, nylon, or combinations thereof. In some embodiments, the flexible plastic container 2 is made from metalized plastic sheet to prevent the decomposition of the active ingredients, such as hypochlorous acid, caused by light (UV radiation).

As illustrated in FIGS. 1 and 2, the first compartment 21 and the second compartment 22 are formed as hermetically separate compartments. In some embodiments, the first compartment 21 and the second compartment 22 are separated by a sealing portion 3 formed across the flexible plastic container 2. The sealing portion 3 may be formed by, for example, adhesives or heat sealing. As illustrated in FIGS. 1 and 2, the sealing portion 3 may be formed as a frangible seal.

The first compartment 21 contains a treating fluid. In some embodiments, the treating fluid is a hypochlorous acid solution such as a water solution of hypochlorous acid. In some embodiments, the treating fluid consists of only water and hypochlorous acid. The concentration of the active ingredients in the treating fluid may be any concentration suitable for the treatment of a pet and contacting human skin. For example, the treating fluid may be a hypochlorous acid solution having a concentration within the range of 0.01% to 0.05% by weight. In some embodiments, the concentration of the hypochlorous acid solution is 0.02% by weight.

Figure 4:
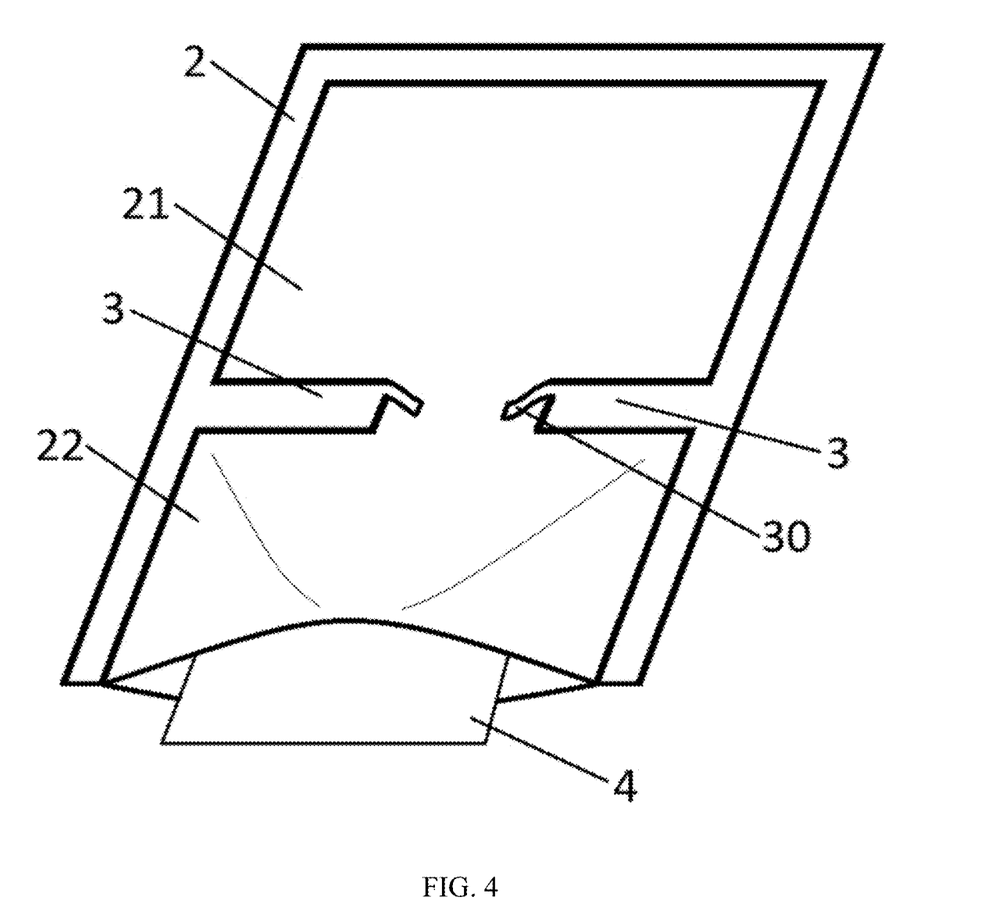
FIG. 4 is a perspective view of the fluid treatment kit shown in FIGS. 1-3, where the breakable seal is broken and a flexible plastic container of the fluid treatment kit is opened.
Figure 5A:
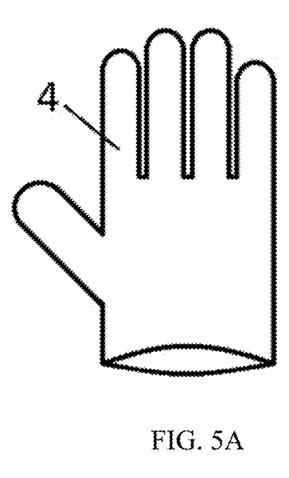
FIGS. 5A-5C are top views of an applicator according to various exemplary embodiments.
Figure 5B:
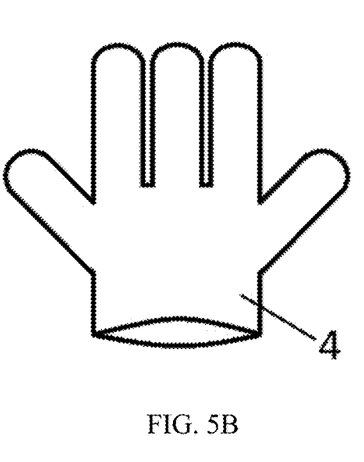
Figure 5C:
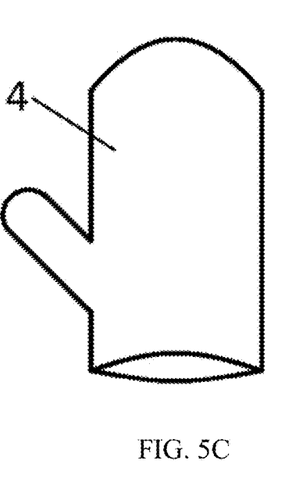

As illustrated in FIG. 4, the second compartment 22 contains at least one applicator 4. In some embodiments, the second compartment 22 contains a pair of applicator 4. The applicator 4 comprises liquid-absorbing materials, for example, cloth wipes, sponges, and swabs. In some embodiments, the applicator 4 comprises non-woven fabric made from polymer fibers. The at least one applicator 4 may be compressed, for example by vacuum packaging, to reduce the volume. As illustrated in FIG. 5A-5C, in some embodiments, the applicator 4 is formed into a glove, such that the applicator 4 can be worn on hand by the user during the treatment of the pet. As illustrated in FIG. 5B, the applicator 4 may be formed into a glove having a symmetric shape, such that the user can conveniently switch between the faces of the applicator 4 on one hand. In some embodiments, the applicator 4 is formed into a glove with five finger pockets having identical shapes. As illustrated in FIG. 5C, the applicator 4 may be formed into a mitten glove. The applicator 4 may be formed into various shapes that can be worn or equipped on the hand.

In some embodiments, the at least one applicator 4 is capable of absorbing substantially all of the treating fluid in the first compartment 21. As such, no liquid will spill out from the flexible plastic container 2 when the flexible plastic container 2 is opened by the user, and no liquid will drop or spill from the applicator 4 when the applicator 4 is used for the treatment of the pet. In some embodiments, the first compartment 21 contains 2 fluid ounces of treating fluid, and the second compartment 22 contains a pair of applicator 4 capable of absorbing 2 fluid ounces of treating fluid in total.

As illustrated in FIGS. 1 and 2, the breakable seal 30 is disposed between the first compartment 21 and the second compartment 22. The breakable seal 30 may be formed by, for example, adhesives or heat sealing. In some embodiments, as illustrated in FIGS. 1 and 2, the breakable seal 30 is formed as part of the sealing portion 3 formed across the flexible plastic container 2, and is narrower than other parts of the sealing portion 3. As such, the breakable seal 30 is the weakest part of the sealing portion 3, and is the part of the sealing portion 3 that breaks first when pressure is applied on the first compartment 21. The breakable seal 30 may have a length within a range of 1 to 5 cm. In some embodiments, the breakable seal 30 has a length of 2.5 cm. In some embodiments, the breakable seal 30 is formed across the whole width of the flexible plastic container 2, such that the breakable seal 30 comprises the entire sealing portion 3.

The breakable seal 30 is breakable by applying pressure to the first compartment 21 containing the treating fluid. In some embodiments, the breakable seal 30 is configured to break under a pressure caused by the user squeezing the first compartment 21, for example, a compressed fluid pressure against the frangible seal of the sealing portion 3. For example, the breakable seal 30 may be configured to break when the first compartment 21 is squeezed with a force within a range of 5 to 400 newtons, including 10 to 350 newtons, 50 to 350 newtons, and 100 to 300 newtons. In some embodiments, the breakable seal 30 is configured to break when the first compartment 21 is squeezed with a force of 300 newtons.

As illustrated in FIGS. 1 and 2, the breakable seal 30 may have a wavy shape or a zigzag shape, in order to assist the breaking of the breakable seal 30. In some embodiments, the breakable seal 30 is breakable by tearing apart the sealing portion 3.

When the breakable seal 30 is broken, as illustrated in FIG. 3, the first compartment 21 and the second compartment 22 are open to, or in communication with, each other. As such, the treating fluid flows from the first compartment 21 into the second compartment 22, and is absorbed by the at least one applicator 4. As illustrated in FIG. 4, the flexible plastic container 2 can be opened, for example by tearing off one end, such that the user can remove the applicator 4 and use it for the treatment of the pet.

Figure 6A:
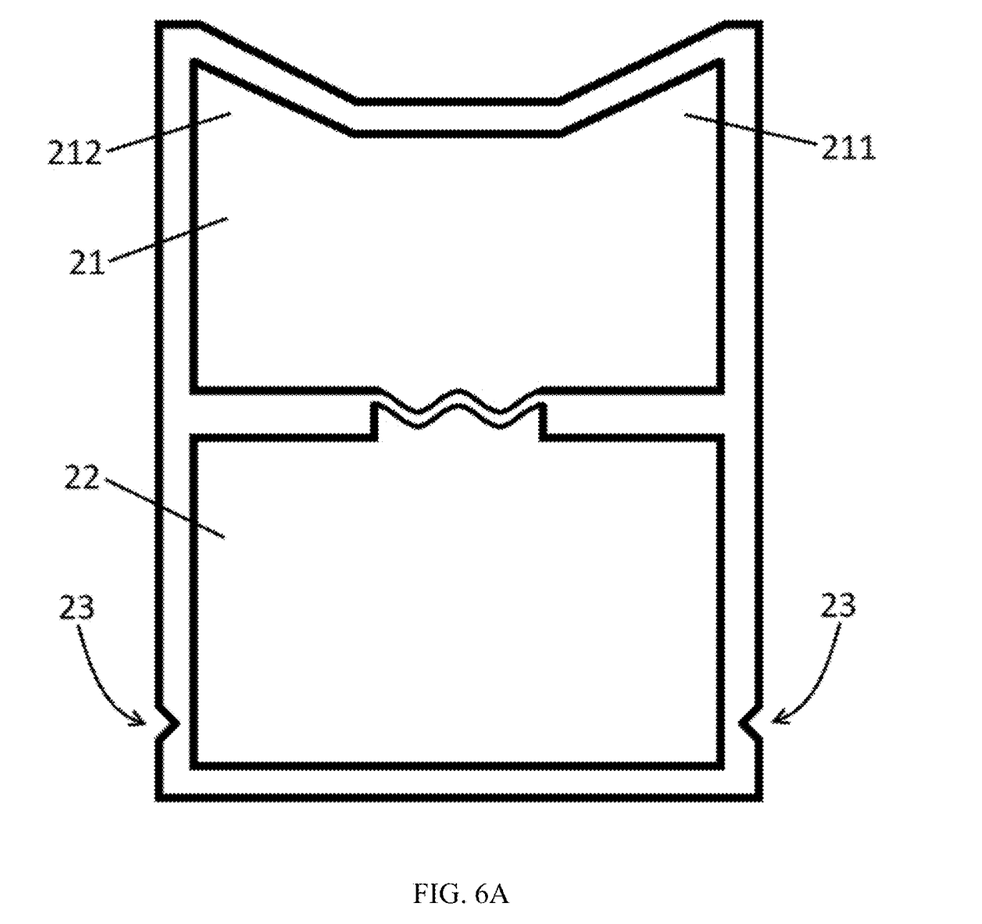
FIGS. 6A and 6B are top plan views of a fluid treatment kit according to an exemplary embodiment.
Figure 6B:
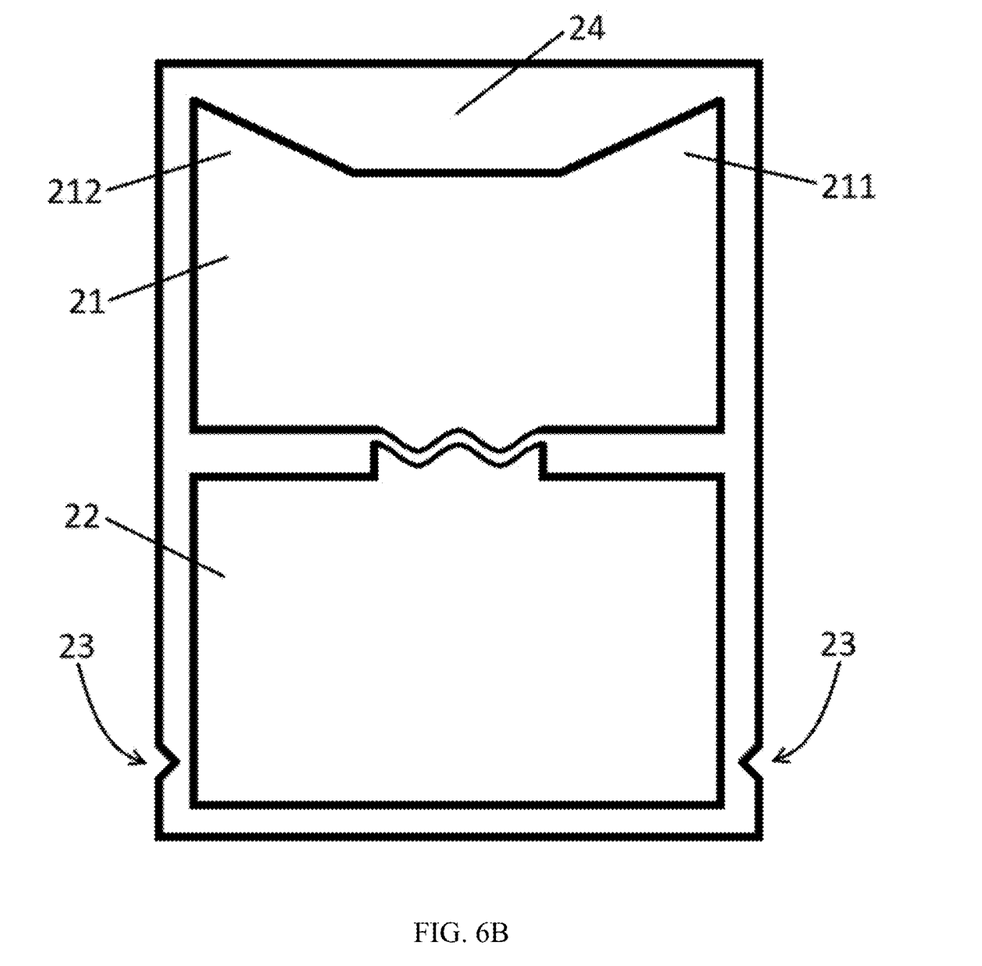

As illustrated in FIGS. 6A and 6B, in some embodiments, the first compartment 21 may be formed with two ear-shaped portions 211 and 212. The ear-shaped portions 211 and 212 may allow the user to grab and squeeze the first compartment 21 more easily. The user may also cut through the ear-shaped portions 211 and 212, and use the ear-shaped portions 211 and 212 as a nozzle for pouring out the hypochlorous acid solution for other uses. In some embodiments, as illustrated in FIG. 6B, a trapezoidal flat portion 24 is formed on the flexible plastic container 2. The trapezoidal flat portion 24 may allow the user to carry the fluid treatment kit 1 without accidentally applying pressure on the first compartment 21.

As illustrated in FIGS. 6A and 6B, in some embodiments, the flexible plastic container 2 is formed with one or more cutout 23. The cutout 23 may allow the user to tear open the flexible plastic container 2 and remove the applicator 4. Notches, slits, and/or perforations may additionally or alternatively be used to facilitate tearing.

In operation, the user breaks the breakable seal 30 by applying pressure to the first compartment 21 by, for example, squeezing the first compartment 21. The user may also break the breakable seal 30 by tearing apart the sealing portion 3. As a result, the first compartment 21 and the second compartment 22 are in communication with each other. The treating fluid contained in the first compartment 21 flows into the second compartment 22 and is absorbed by the at least one applicator 4 contained in the second compartment 22. The user opens the flexible plastic container 2, removes the applicator 4, and uses the applicator 4 for the treatment of the pet. In some embodiments, the applicator 4 is formed into a glove, and the user wears the applicator 4 on a hand during the treatment of the pet. For some pets such as cats and dogs, the treatment can be done by petting, wiping, or rubbing movements. In some embodiments, after the treatment, the treating fluid on the pet's body can be air dried. For example, hypochlorous acid solution can be air dried when included in the fluid treatment kit 1 as the treating fluid.

Figure 7:
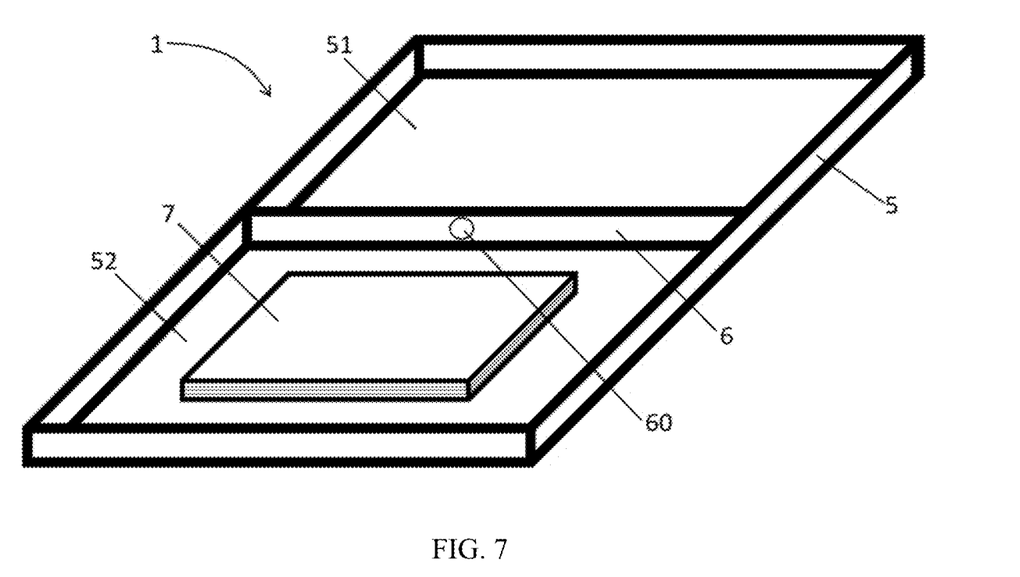
FIG. 7 is a perspective view of the internal structure of a fluid treatment kit according to an exemplary embodiment.
Figure 8:
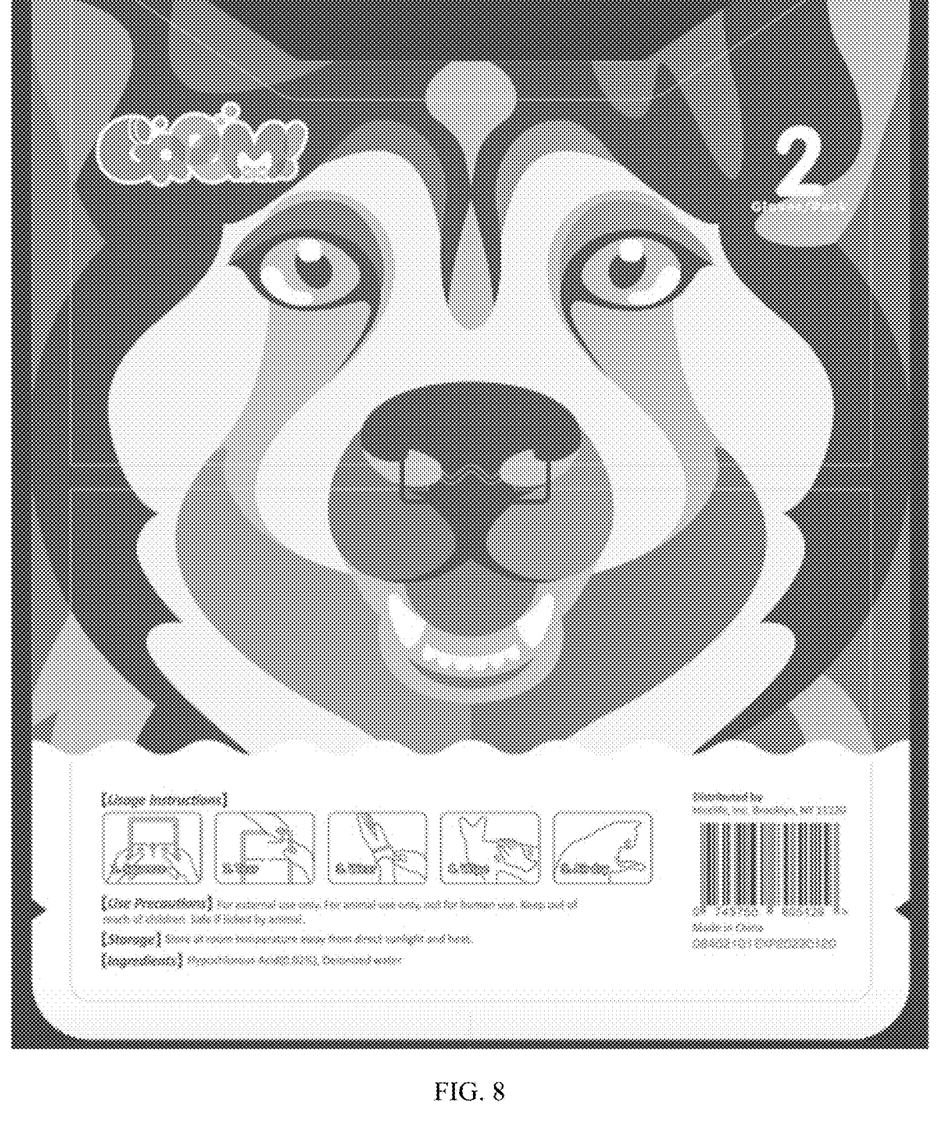
FIG. 8 is a top plan view of a pet cleaning product according to the present disclosure.

As illustrated in FIG. 7, in some embodiments, the fluid treatment kit 1 comprises a container 5. In some embodiments, the container 5 is a plastic bag. In various embodiments, the container 5 may comprise various flexible or rigid plastic materials. The container 5 defines a first compartment 51 and a second compartment 52. The first compartment 51 contains a treating fluid (not shown). In some embodiments, the treating fluid is a hypochlorous acid solution. The second compartment 52 contains at least one applicator 7. The at least one applicator 7 may be compressed, for example by vacuum packaging, to reduce the volume. A divide 6 is disposed between the first compartment 51 and the second compartment 52. A channel 60 is formed on the divide to communicate the first compartment 51 and the second compartment 52. In some embodiments, the channel 60 is attached with a breakable seal (not shown). The breakable seal is configured to break when pressure is applied on the first compartment 51, allowing the treating fluid to flow into the second compartment 52 through the channel 60. In some embodiments, the channel 60 is attached with a valve (not shown). The valve may be configured to allow the treating fluid to pass through when pressure is applied on the first compartment 51. The user may apply pressure to the first compartment 51 by for example, squeezing or pressing the first compartment 51. The at least one applicator 7 comprises liquid-absorbing materials and absorbs the treating fluid flowing into the second compartment 52. The user takes the applicator 7 out of the container 5 through a window or slit (not shown) formed on the second compartment 52, and uses the applicator 7 for the treatment of the pet.

In some embodiments, the first compartment 51 is configured to receive a replaceable treating fluid container. The replaceable treating fluid container may comprise a plastic container suitable for storing the treating fluid, such as a flexible plastic bag or box. The replaceable treating fluid container may comprise an adaptor, and attaches to the channel 60 through the adaptor. As such, the treating fluid can be supplied, when there is an inadequate amount in the first compartment 51, by replacing the replaceable treating fluid container.

In some embodiments, the second compartment 52 is configured to receive a replaceable applicator container. The replaceable applicator container may comprise a plastic bag or box. The replaceable applicator container may comprise an adaptor, and attaches to the channel 60 through the adaptor. As such, the applicator 7 can be supplied, when there is an inadequate amount in the second compartment 52, by replacing the replaceable applicator container.

The invention claimed is:

1. A fluid treatment kit comprising a flexible plastic container defining a first compartment and a second compartment,
   wherein the first compartment contains a treating fluid,
   wherein the second compartment contains at least one applicator,
   wherein a breakable seal is disposed between the first compartment and the second compartment,
   wherein the breakable seal is breakable to allow the treating fluid to flow into the second compartment,
   wherein the at least one applicator comprises liquid-absorbing materials and absorbs the treating fluid flowing into the second compartment,
   wherein the treating fluid is a water solution of hypochlorous acid having a concentration of 0.02% by weight, a length of the breakable seal is 2.5 cm, a divide is disposed between the first compartment and the second compartment, a channel is formed on the divide to communicate the first compartment and the second compartment, the channel is attached with the breakable seal and a valve, the valve is configured to allow the treating fluid to pass through when pressure is applied on the first compartment.

2. The fluid treatment kit according to claim 1, wherein the at least one applicator comprises non-woven fabric made from polymer fibers.

3. The fluid treatment kit according to claim 1, wherein the at least one applicator consists of a pair of applicators.

4. The fluid treatment kit according to claim 1, wherein each of the at least one applicator is formed into a glove.

5. The fluid treatment kit according to claim 1, wherein each of the at least one applicator is formed into a glove having a symmetric shape.

6. The fluid treatment kit according to claim 1, wherein the at least one applicator is capable of absorbing all of the hypochlorous acid solution.

7. The fluid treatment kit according to claim 1, wherein the breakable seal is formed by heat sealing.

8. The fluid treatment kit according to claim 1, wherein the breakable seal is breakable by applying pressure to the first compartment.

9. The fluid treatment kit according to claim 1, wherein the breakable seal is breakable by squeezing the first compartment.

10. The fluid treatment kit according to claim 1, wherein the first compartment is formed with two ear-shaped portions.

11. A method for treating a pet, comprising:
providing a flexible plastic container defining a first compartment and a second compartment, the first compartment containing a hypochlorous acid solution, the second compartment containing at least one applicator;
breaking a breakable seal disposed between the first compartment and the second compartment, such that the hypochlorous acid solution flows into the second compartment;
absorbing the hypochlorous acid solution in the at least one applicator;
opening the flexible plastic container to remove the at least one applicator;
treating the pet with the at least one applicator,
wherein the hypochlorous acid solution has a concentration of 0.02% by weight, a length of the breakable seal is 2.5 cm, a divide is disposed between the first compartment and the second compartment, a channel is formed on the divide to communicate the first compartment and the second compartment, the channel is attached with the breakable seal and a valve, the valve is configured to allow the hypochlorous acid solution to pass through when pressure is applied on the first compartment.

12. The method for treating a pet according to claim 11, further comprising:
wearing the at least one applicator on a hand, wherein each of the at least one applicator is formed into a glove.

* * * * *